(12) United States Patent
Moth

(10) Patent No.: US 10,295,450 B2
(45) Date of Patent: May 21, 2019

(54) APPARATUS AND METHODS FOR DETERMINING GRAVITY AND DENSITY OF SOLIDS IN A LIQUID MEDIUM

(71) Applicant: Red Meters LLC, Orlando, FL (US)

(72) Inventor: David J. Moth, Orlando, FL (US)

(73) Assignee: Red Meters LLC, Orlando, FL (US)

( * ) Notice: Subject to any disclaimer, the term of this patent is extended or adjusted under 35 U.S.C. 154(b) by 80 days.

(21) Appl. No.: 15/237,033

(22) Filed: Aug. 15, 2016

(65) Prior Publication Data

US 2017/0045432 A1      Feb. 16, 2017

Related U.S. Application Data

(60) Provisional application No. 62/204,727, filed on Aug. 13, 2015.

(51) Int. Cl.
*G01N 9/00* (2006.01)
*G01N 9/04* (2006.01)
*G01N 11/00* (2006.01)

(52) U.S. Cl.
CPC ....... *G01N 9/04* (2013.01); *G01N 2011/0013* (2013.01)

(58) Field of Classification Search
None
See application file for complete search history.

(56) References Cited

U.S. PATENT DOCUMENTS

| | | | |
|---|---|---|---|
| 2,432,039 A | 12/1947 | Plank | |
| 4,140,292 A * | 2/1979 | Kaigler, Jr. | F16L 3/16 248/49 |
| 4,745,807 A * | 5/1988 | O'Neill | G01N 9/06 73/434 |
| 4,876,879 A * | 10/1989 | Ruesch | G01F 1/74 73/32 A |
| 5,041,990 A | 8/1991 | Yabumoto et al. | |

(Continued)

FOREIGN PATENT DOCUMENTS

| CN | 101084416 | 6/2010 |
|---|---|---|
| DE | 10340555 | 9/2004 |

(Continued)

OTHER PUBLICATIONS

PCT International Searching Authority; International Search Report and Written Opinion dated Oct. 31, 2016; entire document.

(Continued)

*Primary Examiner* — Paul M. West
*Assistant Examiner* — Mark A Shabman
(74) *Attorney, Agent, or Firm* — Foley & Lardner LLP

(57) ABSTRACT

Apparatus and methods for the continuous measurement of specific gravity or density of solids in a fluid medium are disclosed. A system for continuous measurement of density of a flowing medium comprises a cartridge connected in series to an inflow pipe and an outflow pipe, a displacement sensing device adapted to monitor displacement changes of the cartridge when a medium flows through the cartridge, a base configured to provide a support for the displacement sensing device, a pressure sensor, a temperature sensor, and a processor configured to calculate density of the flowing media based on measured displacement change, temperature and pressure.

27 Claims, 7 Drawing Sheets

(56) References Cited

U.S. PATENT DOCUMENTS

| | | |
|---|---|---|
| 6,769,299 B2 | 8/2004 | Forster et al. |
| 7,290,447 B1 | 11/2007 | Burnette et al. |
| 9,393,793 B2 | 7/2016 | Nakamura et al. |
| 9,446,585 B2 | 9/2016 | Goyal et al. |
| 2004/0190177 A1 | 9/2004 | Christie et al. |
| 2007/0089483 A1 | 4/2007 | Kriel |
| 2017/0016753 A1 | 1/2017 | Shi et al. |

FOREIGN PATENT DOCUMENTS

| | | |
|---|---|---|
| EP | 0 722 084 A1 | 7/1996 |
| JP | H07253373 | 10/1995 |
| JP | 2009538790 | 11/2009 |
| KR | 101338175 | 12/2013 |
| WO | WO2012118775 | 9/2012 |
| WO | WO-2015/069100 A2 | 5/2015 |

OTHER PUBLICATIONS

AW-Lake Company, Lake Monitors, Liquid Flow Meters Installation, Operating & Maintenance Manual, 2016, 16 pgs.

Roskos, K. et al, "Simple System for Isothermal DNA Amplification Coupled to Lateral Flow Detection." PLOS One, vol. 8, Issue 7, Jul. 2013, 8 pgs.

Extended European Search Report dated Feb. 22, 2019 in related European Appl. 16836026 (10 pgs.).

\* cited by examiner

**From inside(1) to outside(10)

1: 1/4" Tan Natural Gum Rubber, 40A durometer
2: Steel flange
3: First layer Kevlar
4: Second layer Kevlar
5: 1/8" Tan Natural Gum Rubber
6: 3/4" pitch Steel wire reinforcement, embedded into (5)
7: Four evenly spaced carbon fiber rods
8: 1/16" Tan Natural Gum Rubber
9: Third layer Kevlar
10: Outside layer 1/16" Tan Natural Gum Rubber

APPARATUS AND METHODS FOR DETERMINING GRAVITY AND DENSITY OF SOLIDS IN A LIQUID MEDIUM

CROSS-REFERENCE TO RELATED APPLICATION

This application claims the benefit of U.S. Provisional Patent Application Ser. No. 62/204,727, filed on Aug. 13, 2015, the contents of which are herein incorporated by reference in their entirety.

FIELD OF THE INVENTION

The present invention relates to the field of measurement devices, and more particularly, to devices and methods for the continuous real-time measurement of the density of a continuous medium flowing through a meter.

BACKGROUND TO THE INVENTION

Nuclear measurement devices have been used to measure the density of a medium flowing through a meter. Present devices, however, have many drawbacks, for instance, an inability to make measurements in real-time, a lack of consistency in measured values and a limited range of application, typically liquid flowing through a metal pipe. The devices also come with many safety restrictions. Nuclear meters cannot be transported without proper paperwork, and there are restrictions on the transport of nuclear materials. The dredging industry cannot use nuclear density meters on ships because nuclear sensors are not meant to be moved. Nuclear meters also suffer from being able to measure only a single column of fluid defined by the diameter and longitudinal length of a pipe. The volume measured is necessarily small, and nuclear density meters measure in one spatial direction only. The density of a fluid can, however, vary substantially within the cross-section of a pipe. Nuclear sensors are subject to stringent safety and security standards. Current nuclear density meters have about 80% accuracy with a wait time between measurements of 2-10 minutes.

Other techniques for measuring the density of a continuously flowing medium are known. Ultrasound and microwave sensors, for example, also suffer from being able to measure only a fraction of a cross section of pipe and being limited by a maximum pipe diameter. The signal from these measurement techniques becomes irregular noise above about 15% solids. These measurement devices can have probes that are exposed to the medium making them undesirable for applications involving highly corrosive or abrasive media as one finds, for example, in the mining and dredging industries. Microwave sensors are limited to media with a consistent electrical relative permittivity and a high conductivity.

Auto-sampling has been used to measure the density of continuous flowing media. In this approach multiple samples are obtained throughout a testing period for density measurement in a lab environment. Evaporation en route to the testing facility can occur, however, leading to an overestimate of the percent solids of the slurry sampled. Another drawback to auto-sampling is the wait time. It can take up to 24 h or more to obtain a single reading, which is unacceptably long in many industries. This approach to sampling is also limited to small volumes. This increases the odds the measurement will accurately measure the sample but not the system from which the sample was obtained.

A Coriolis meter has been used to measure the density of a fluid medium in a pipe. Such meters make use of a thin-walled bent pipe. Medium flowing through the bend causes it to vibrate. Measurement of the phase shift in vibration frequency at the end of the bent pipe enables measurement of the mass flow rate. Abrasive slurries like those common to the mining industry erode the bent pipe within weeks, or in some cases days. Another disadvantage of these meters is the small inner diameter of the bent pipe.

Current fluid density measurement techniques display a variety of limitations. They are therefore less useful than desired in industries such as mining, dredging and waste water management. Accordingly, it would be beneficial to these industries to provide an apparatus and methods that provide accurate, repeatable, highly resolved, continuous and real-time sensing and measurement of the density of a fluid medium flowing through a meter and avoid the drawbacks noted above.

SUMMARY OF THE INVENTION

In view of the foregoing, it is an object of the present invention to provide an apparatus and methods for continuously measuring the density and specific gravity (SG) of liquids flowing through a meter. The liquids can include abrasive slurries, pastes and sludges. According to one embodiment of the present invention, an apparatus adapted for continuous measurement of SG of a liquid flowing through a meter includes a cartridge connected serially between an inflow pipe and an outflow pipe. The apparatus further comprises a displacement sensing device adapted to monitor displacement changes of the cartridge as a liquid flows through the cartridge. A base is configured to provide support for the displacement sensing device. The inflow and outflow pipes are supported by a plurality of mounting beams connected to the ground. The apparatus also comprises a pressure sensor and a temperature sensor. The apparatus further comprises a processor configured to calculate density, SG and other parameters of a flowing medium based on the measurement of displacement, temperature and pressure.

DETAILED DESCRIPTION OF THE INVENTION

The invention will now be described in greater detail with reference to the previously mentioned drawings and figures.

The description may, however, be merely an embodiment of one configuration of such a system. The description should not be construed as limited to the embodiments set forth herein. The embodiments are intended merely to provide a thorough and complete sense of the scope of the invention. A single pipe diameter is described, but it will be obvious to one of ordinary skill in the art that the principles expressed herein will be no less suitable for smaller and larger diameters as stated.

It should be noted that in the present description the terms "upper", "lower", "front", "vertical", "horizontal" and derivatives thereof relate to FIGS. 1-4 and the orientation of objects described therein. Also, the term "medium" should be understood to represent a plethora of suitable materials, including liquids, slurries, ashes, sludges, oils or any similar substances.

Figure 1:
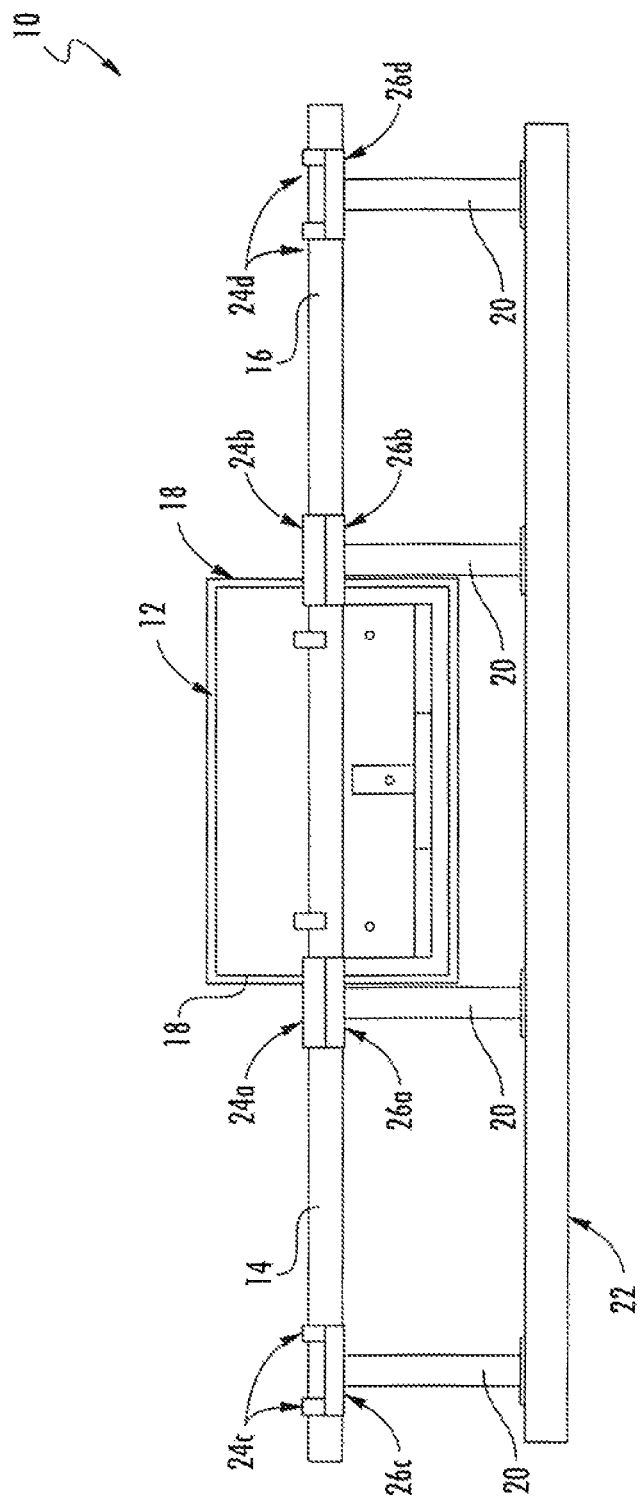
FIG. 1 is a side view of an apparatus setup for continuously measuring density and SG in a flowing media, according to one embodiment of the present invention.

Referring to FIG. 1, a system 10 for the continuous measurement of density and related parameters of a flow medium includes a measurement apparatus (not shown) placed in an enclosure 12 with a horizontal inflow pipe 14 and an outflow pipe 16 passing through respective sidewalls 18 of the enclosure 12. The inflow pipe 14 and the outflow pipe 16 are respectively connected to an inlet port and an outlet port of a measurement apparatus inside the enclosure 12. The inflow and outflow pipes 14 and 16 are supported by a plurality of vertical support beams 20 connected to the ground 22. The inflow and outflow pipes 14 and 16 are secured to support beams 20 via upper brackets 24a, 24b, 24c and 24d, lower brackets 26a, 26b, 26c and 26d, and appropriate fasteners, e.g. bolts. The ground 22 is preferably made of concrete. The ground 22 can also be built on a movable base such that the apparatus assembly can be portable.

Two pipe support beams 20 are sufficient to reduce the vibrations of the system 10. More than two, however, e.g. four, could be more desirable. The support beams 20 are preferably made out of carbon steel for its ease of manufacture and sturdiness. Other materials with suitable mechanical properties can substitute for carbon steel.

The enclosure 12 is suspended above the ground 22 to reduce effects of vibration from the ground. In one embodiment, the innermost brackets (e.g. 24a, 24b, 26a, 26b) include respective flanges that can be attached to respective end walls (not shown) connected to the measurement apparatus (not shown). The outermost supports (e.g., 24c, 24d, 26c, 26d) are used to further dampen the vibrations of the system 10.

The system 10 also includes a temperature measuring device and a pressure measuring device (not shown) inside the enclosure 12 to measure the working conditions of the measurement apparatus.

Figure 2:
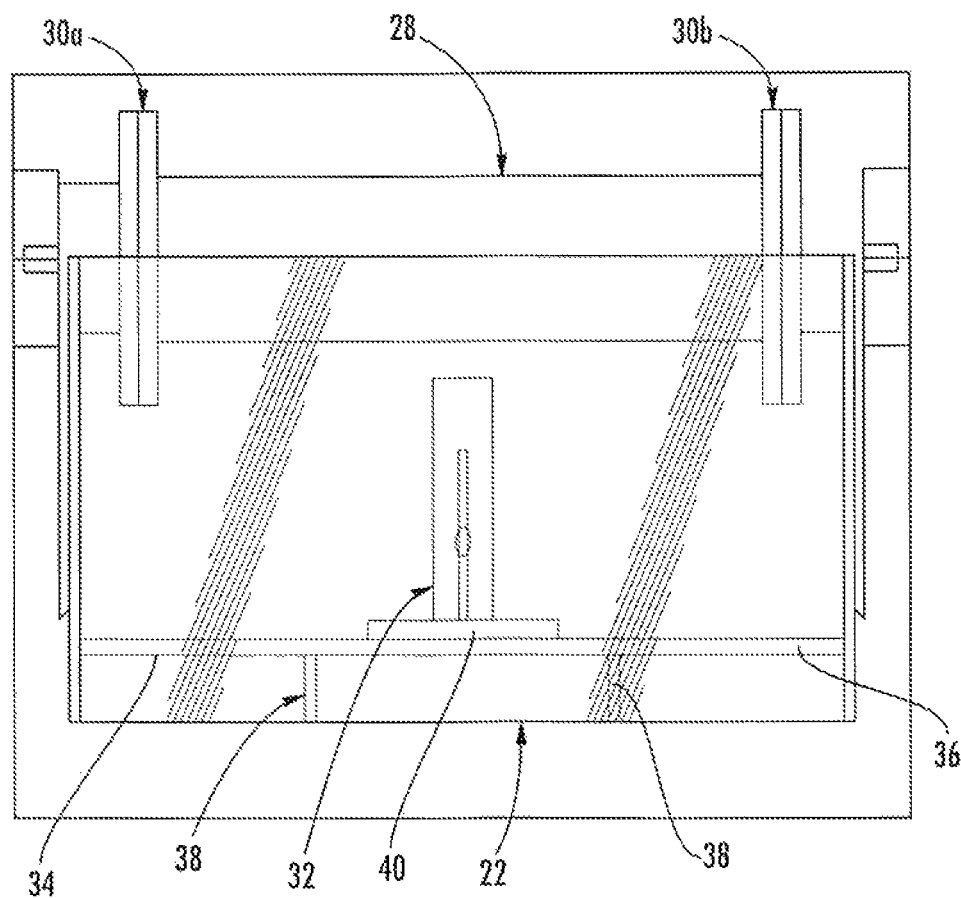
FIG. 2 is a cross sectional view of the apparatus setup of FIG. 1.

Referring to FIG. 2, according to one embodiment of the present invention, an apparatus for measuring the density or SG of a flowing medium includes a cartridge 28 serially connected with the inflow pipe 14 and the outflow pipe 16 with waterproof and pressure-proof connections. The cartridge 28 is made of flexible material (e.g., rubber) such that vertical displacement will occur when a medium flows through. In one embodiment, the inflow and outflow pipes 14 and 16 are connected to the inlet and outlet ports of the flexible cartridge 28 via flanges 30a and 30b. As an example, American National Standards Institute (ANSI) flanges and associated gaskets and fasteners can be used.

The measurement apparatus also includes a displacement measurement device 32 mounted on a base 34. The displacement measurement device 32 is preferably mounted underneath the center of the cartridge 28. In one embodiment, the displacement measurement device 32 includes a high-precision and high-speed laser-based displacement sensor. This sensor can accurately measure the displacement/deflection of the cartridge 28 by a national institute of standards and technology (NIST) traceable weight. Other suitable displacement measurement devices 32 can also be used.

Figure 4:
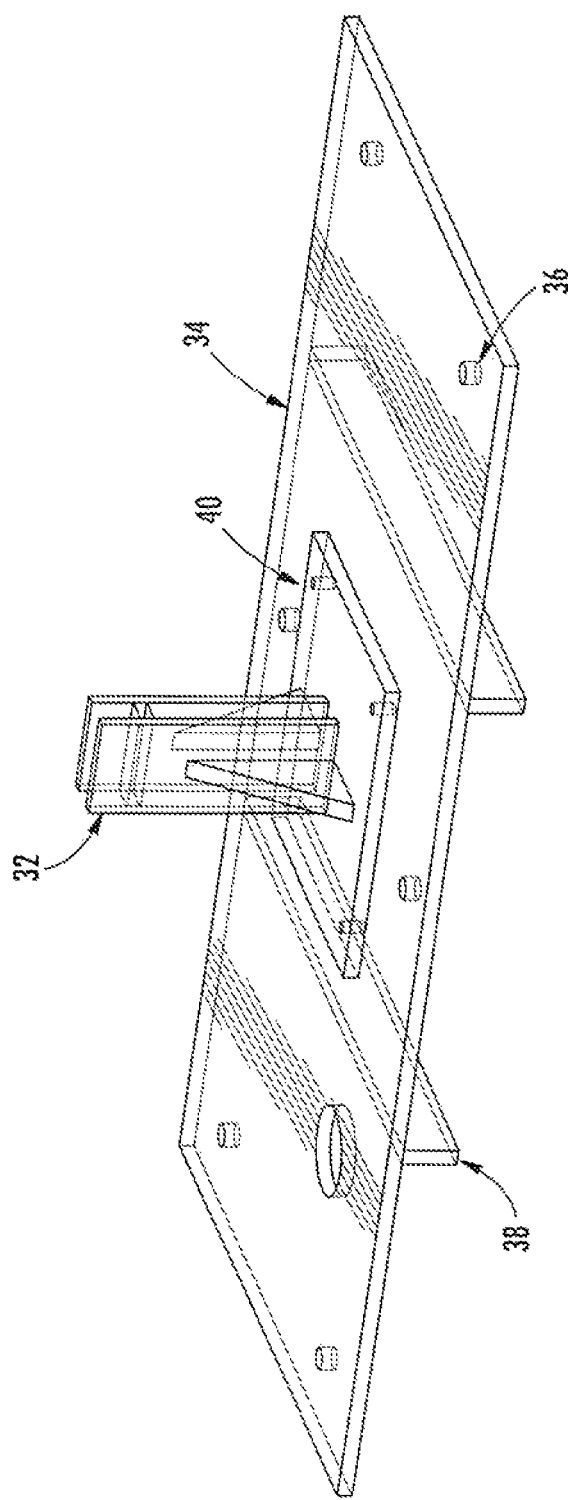
FIG. 4 is a perspective view of a base and a displacement measurement device mounted thereon.

Referring to FIGS. 2 and 4, the base 34 includes a flat portion 36 and at least two mounting posts 38 affixed at the bottom of the flat portion 36, preventing the flat portion 36 from bowing. The base 34 includes a mounting support 40 attached at the top of the flat portion 36 for mounting the displacement measurement device 32 thereon. Suitable fasteners, e.g. bolts or brackets, can be used further to secure the displacement measurement device 32 on the mounting support 40. The base 34 is made of a material with a low coefficient of thermal expansion (CTE), such as tempered glass. Both the mounting post 38 of the base 34 and the plurality of support beams 20 for supporting inflow and outflow pipes are connected to the ground 22 to minimize the effects of vibration of the inflow pipe 14 and/or outflow pipe 16 on the displacement measurement 32. In addition, rubber fittings or similar fittings can be placed at connection points between components to further reduce vibrations.

Figure 3:
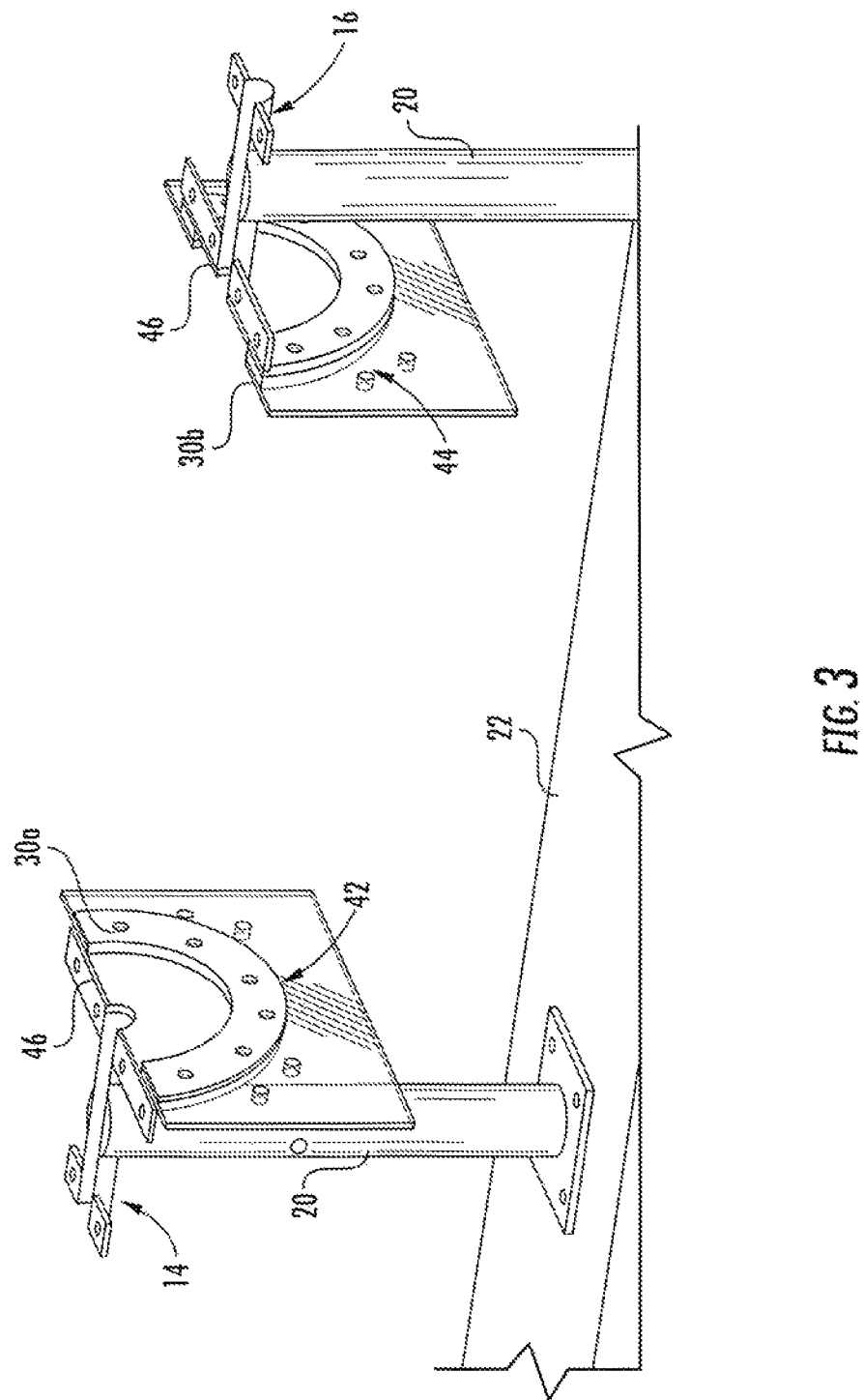
FIG. 3 is a perspective view of the pipe supports and mount for a flexible cartridge of the apparatus of FIG. 2, according to one embodiment of the present invention.

Referring to FIG. 3, in the depicted embodiment, flange 30a and 30b are connected (e.g., welded, bolted) to inflow pipe 14 and outflow pipe 16 at respective end walls 42 and 44, wherein the end walls 42 and 44 are affixed to respective support beams 20. The flanges 30a and 30b are attached to the respective end walls 42 and 44 with at least one gasket 46 (e.g. made of rubber) mounted therebetween. The gaskets 46 can reduce vibrations transferred to the end walls 42 and 44 and prevent end walls 42 and 44 (e.g. made of glass) from making direct contact with the flanges 30a and 30b (e.g. made of metal). The end walls 42 and 44 are made of material with a low CTE, such as tempered glass, which can minimize effects due to temperature fluctuations on the displacement of the cartridge 28. The displacement/deflection is usually on the micron length scale, making thermal expansion/contraction a significant concern. Vibrations due to pumping liquid, slurry or sludge through the inflow pipe and outflow pipe 14 and 16 are another significant source of noise. To minimize this noise, the end walls 42 and 44 are mounted to the respective support beams 20 which are in turn connected to the ground 22. The innermost bracket supports (shown in FIG. 1 as 24a, 24b, 26a and 26b) are connected to the end wall 42 and 44 to minimize vibrations.

Figure 5:
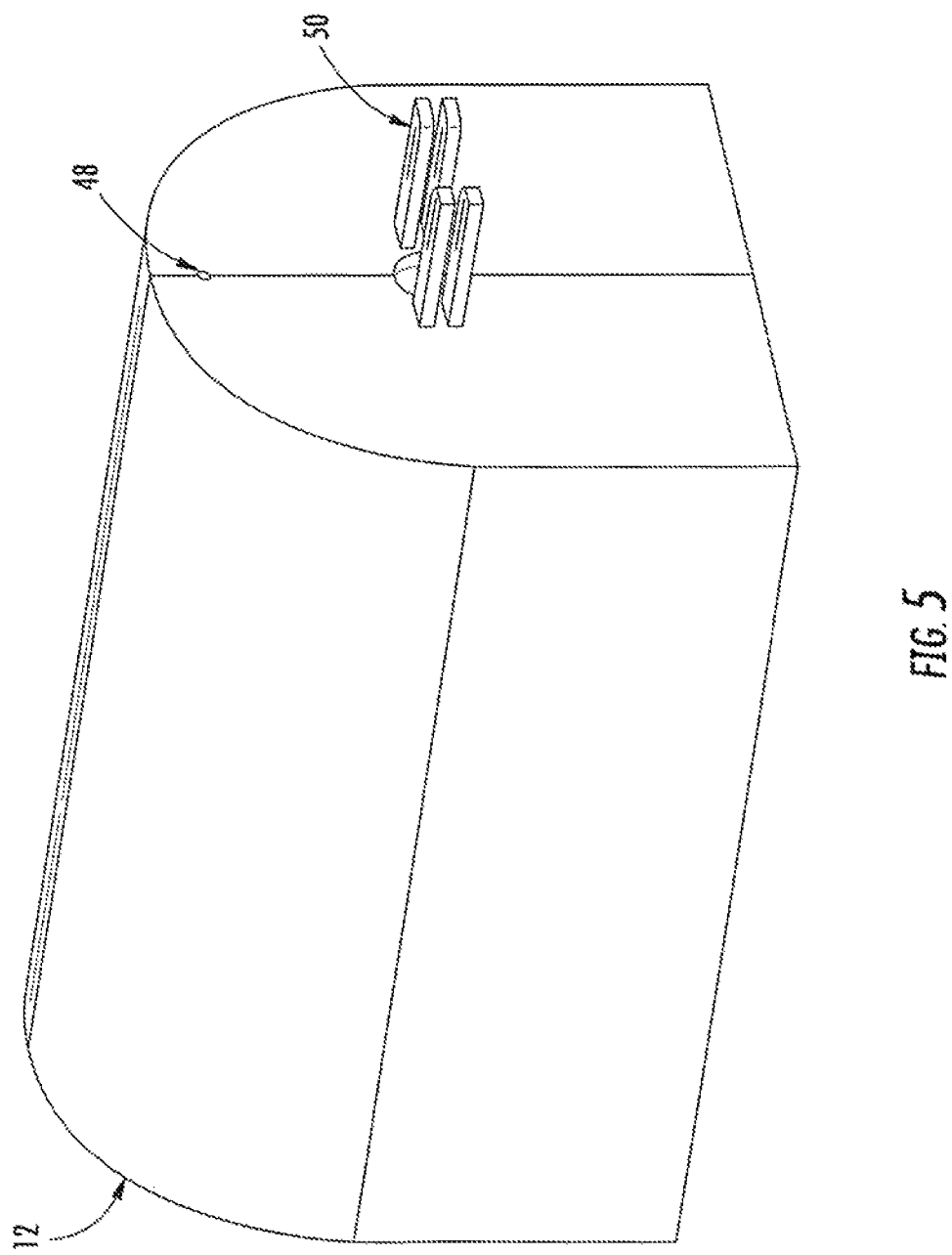
FIG. 5 is a perspective view of an enclosure for the measurement apparatus.

Referring to FIGS. 1 and 5 the measurement apparatus is placed inside an enclosure 12. Preferably, the enclosure 12 is made of low electrical conductivity material such as aluminum. The enclosure 12 will preferably have a smooth surface with a curved top to be more aerodynamic and thus prevent the accumulation of rain or snow. The enclosure 12 can also minimize temperature and humidity fluctuations and effects due to wind, rain and other weather conditions. The measurement apparatus, when in use, is placed inside the enclosure 12 with inflow and outflow pipes 14 and 16 passing through openings 46 on respective sidewalls of the enclosure 12. The base 34 (not shown in FIGS. 1 and 4) of the displacement measurement device 32 is placed on the bottom of the enclosure 12. A lock 48 (e.g. a cam lock) can further secure and seal the enclosure 12 and attachment apparatus 50 for affixing the enclosure 12 to a specific location.

The enclosure 12 can minimize the effects of outside temperature and humidity on the measurement. The enclosure 12 is preferably light-weighted, reducing the strain on the system 10. The enclosure 12 is easily accessible and installed, therefore reducing the cost of maintenance.

After an accurate measure of the displacement of cartridge 28 is obtained, a weight value can be calculated. This value can be used to calculate the density given a cartridge volume, SG can be calculated from the density, and SG can be used to calculate percent solids in a media material and mass flow rate of the media.

A pressure sensor (not shown) is used to monitor the pressure in proximity to the cartridge 28 and the distance measurement device 32 in case of leaks and breakages in the apparatus. For example, a pressure reading of zero will indicate a leak in the system 10. A large pressure rise can burst the cartridge or increase measurement uncertainty. Safety measures are implemented to ensure that the pressure is controlled. The pressure sensor can serve as an alarm in case of a large pressure deflection. In one embodiment, a wear sensor can be installed inside the cartridge 28 to indicate the utility of the cartridge 28. The pressure sensor, the temperature sensor, and/or the displacement measurement device 32 reading outside of an expected range can flag checking the components of the apparatus.

The cartridge 28 is light-weighted, making its mass negligible compared to the fluid medium within. The cartridge 28 is also flexible, so that it will deflect by an amount that scales with its weight. The cartridge 28 is preferably made of material with a low thermal expansion to minimize the effect of temperature, for example, Kevlar fabric. This light-weighted material is highly resistant to temperature fluctuations. In one aspect, an abrasion-resistant liner (e.g. a resistant rubber) is placed inside the cartridge 28, allowing measurement of the density of an abrasive slurry. The liner will extend the lifetime of the cartridge. Deflection/displacement of the cartridge 28 can be detected and quantified by the displacement measuring device 32. The deflection can be translated to a force, and a weight can be calculated based on the force. If the cartridge 28 is not able to recover its original shape after the weight of a fluid is removed, the displacement measurement will not be accurate. A constant baseline reference can be used to increase the accuracy of real-time density measurements.

Figure 6:
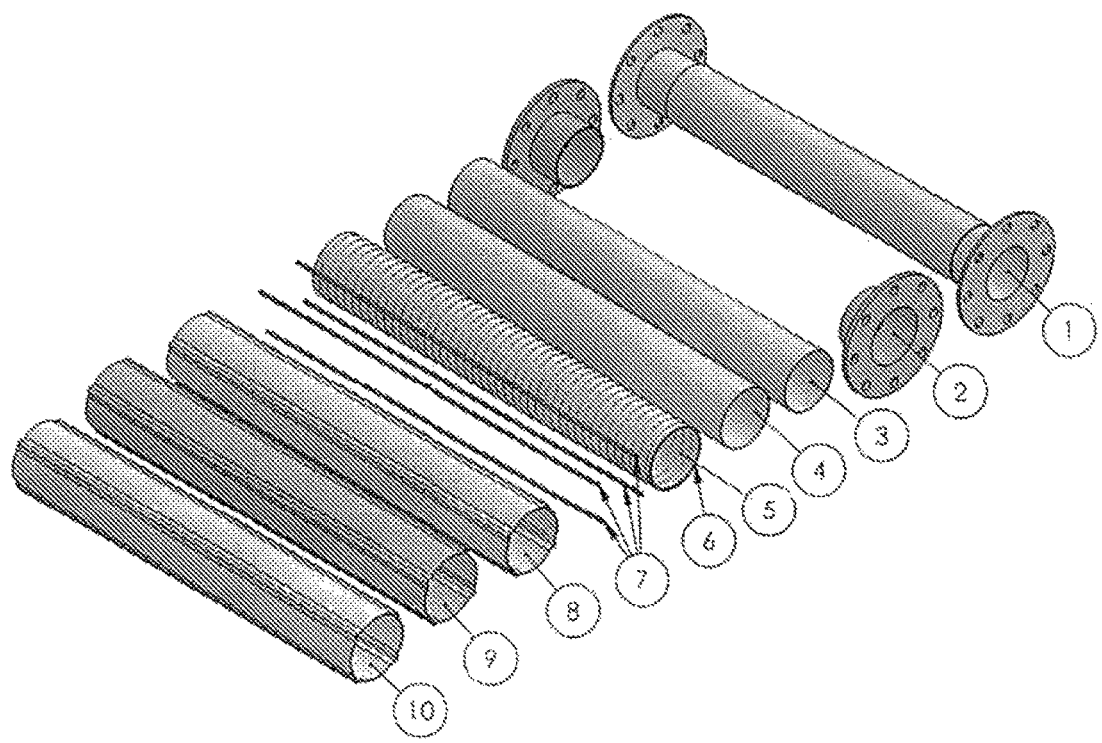
FIG. 6 is an exploded view of the cartridge of the apparatus of FIG. 2, according to one embodiment of the present invention.

Referring to FIG. 6, an exploded view of the cartridge 28 is shown. As shown in the exemplary embodiment illustrated in FIG. 6, the cartridge may include two flanges 2. A conduit is formed between the flanges by a first layer of KEVLAR 3, a second layer of KEVLAR 4, a layer of natural gum rubber, steel wire reinforcement 6 embedded in the rubber layer, fiber carbon rods 7, a layer of natural gum rubber 8, a third layer of KEVLAR 9, and an outside layer of natural gum rubber 10. The cartridge 28 can be configured to resist pressure change as pressure can change the flexibility of the cartridge 28. A pressure control system can be implemented inside the cartridge 28. In an aspect, a helical wire is implanted in the wall of the cartridge 28. The pitch of the wire will have a direct impact on the flexibility of the cartridge 28. The wire can also provide resistance to vacuum-like conditions and maintain the shape of the cartridge, important accurate readings. In another aspect, a plurality of high-modulus (i.e. mechanically stiff) tubes (or rods as illustrated in FIG. 6 by rods 7) are inlaid directly in the wall of the cartridge. These tubes are positioned at points rotated 45°, 135°, 225° or 315° about an axis coincident with the centerline of the cartridge. The high modulus tubes or rods enable the cartridge to return to a reliable zero point, that is, the position of the cartridge given the weight of the cartridge plus the weight of the liquid inside. The number and thickness of the tubes or rods can be altered for different applications. The tubes or rods are not only affixed to the wall of the cartridge itself but also to the flange (e.g., built in rubber flange) connections. Fixed points allows the tubes/rods to flex and encourages the cartridge to return to a defined location. The high modulus tubes/rods can be made of carbon fiber tubes/rods or other suitable materials.

In one embodiment, the inlet and outlet ports have raised sections above the cartridge to prevent air from entering the cartridge 28. The raised portion of the inflow and outflow is at a specific distance away from the flexible cartridge (e.g. more than 5 pipe diameters) to achieve the regular velocity profile.

Figure 7:
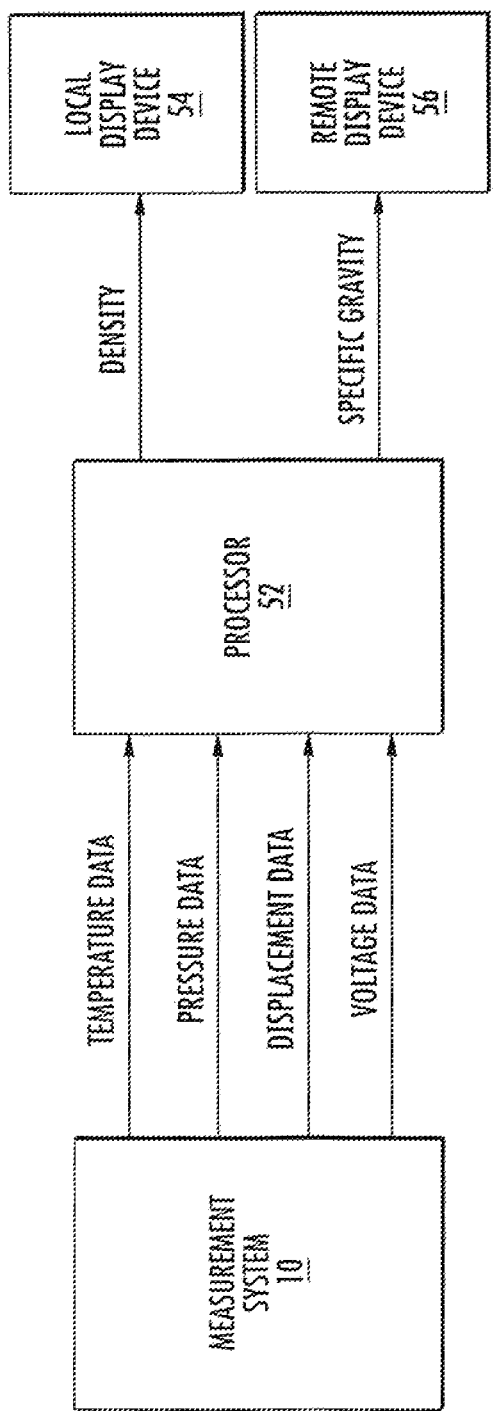
FIG. 7 is a diagram illustrating an example system for continuously measuring density and SG in a flowing media, according to one embodiment of the present invention.

Referring to FIG. 7, a processor 52 is connected to the different components of the system 10 to collect corresponding data, such as temperature, pressure, laser sensor voltage, weight, force, and the like. The collected data can be used to calculate density, SG and related quantities. The collected data and calculated values can be displayed on a local display device 54 and/or a remote device 56 (e.g., a smart phone). The data can be displayed as graphics, tables, numbers or other suitable formats. The local display device 54 can be placed in a housing that satisfy standard National Electrical Manufacturers Association (NEMA) requirements. This housing can protect the measurement system from the effects of weather, fire and dust and other adverse conditions.

As the media travels through the cartridge 28, the cartridge will flex and most visibly at the center point. The flex is determined by measuring distance between, for example, from the top of the high precision displacement laser to the bottom of the cartridge 28. The distance is usually in micrometers. The distance between the laser and cartridge is converted into a weight which is a constant relationship determined during calibration for each specific cartridge. Weight is then converted to SG.

Displacement and weight correlation can be determined empirically for each device. For example, weight is applied to the cartridge 28 and thereby deflect the cartridge 28. The test can be a clear water test. Specifically, known amount of clear water was applied to simulate cartridge displacement for multiple times. This purpose of the process is to identify a baseline and determine that there is no mechanical drift. By repeatedly applying known amount of weights during a series of clear-water testing, the displacement for a given weight is determined. Then weight can be converted to density by dividing the weight by the cartridge volume, such as the grams per cubic centimeter, which is an equivalent term to specific gravity. The SG can be calculated using the formula below:

$$SG = (observed\ reading - expected\ reading) * displacement\ to\ density$$

Thermal Compensation

Thermal compensation for the system is determined through three methods. First method is physical compensation. The system includes a thin but effective insulation to reduce atmospheric temperature effects on the cartridge and the base 34 of the displacement measurement device 32. Second is a temperature correction algorithm. The base 34 of the displacement measurement device 32 and cartridge 28 have predictable expansion profiles as their temperatures change. The third compensation method is to detect and negate effects on support structures of the system. The innermost pipe bracket (e.g. 24a, 24b, 26a, 26b) have main influence on whether the cartridge 28 and base 34 are mounted in parallel and/or if there is torque affecting readings of the displacement measurement device 32. The temperature difference between those the pipe support bracket and the base 34 is an accurate gauge of how much a raw reading would be.

Pressure Compensation

With a primarily rubber cartridge, fluid pressure will affect the inner diameter of the cartridge 28. There are limits to how far the rubber can compress bulge or implode before other physical factors of the cartridge construction become dominant, however those are beyond the 150 PSI (roughly 10 bar) engineering limit on the rest of the system components. Within the expected operation range, pressure can make a small, consistent, and linear effect on total cartridge volume.

> Expected reading=baseline+(cartridge temperature/ cartridge temperature compensation value)+ (absolute pipe support temperature difference/ pipe support difference compensation value)+ (pressure change pressure compensation value).

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described and the claims appended hereto.

What is claimed is:

1. A system for continuously measuring density of a flowing media, comprising:
    a cartridge connected serially between an inflow media pipe and an outflow media pipe, the inflow media pipe and the outflow media pipe arranged on opposite sides of the cartridge and oriented along a same direction as the cartridge;
    a displacement sensing device adapted to monitor displacement changes of the cartridge when the media flow through the cartridge;
    a base configured to provide a support for the displacement sensing device;
    a pressure sensor;
    a temperature sensor; and
    a processor configured to calculate density of the flowing media based on measured displacement change, temperature and pressure.

2. The system of claim 1 wherein the inflow media pipe and outflow media pipe are connected to an input and output of the cartridge via respective flanges.

3. The system of claim 2, wherein the respective flanges are attached to respective end walls with at least one gasket mounted therebetween.

4. The system of claim 1, further comprising: a plurality of supporting beams configured to support the inflow and outflow pipes.

5. The system of claim 4, wherein the base and the plurality of supporting beams are connected to an underlying surface.

6. The system of claim 5, wherein the underlying surface is ground.

7. The system of claim 1, wherein the connection point between the inflow pipe and the outflow pipe and the inflow port and outflow port of the cartridge have higher altitude than the cartridge.

8. The system of claim 1, wherein the media comprises at least one of liquids, abrasive slurries, paste, or sludge.

9. The system of claim 1, wherein the cartridge has an internal diameter between 2 and 40 inches.

10. The system of claim 1, wherein the displacement sensing device comprises a laser displacement sensor.

11. The system of claim 1, wherein the cartridge is configured to have a vertical linear displacement proportional to weight of the media flowing therethrough.

12. The system of claim 1, further comprising
    an enclosure for housing the cartridge, the displacement sensing device the base, the pressure sensor and the temperature sensor.

13. The system of claim 1, wherein the cartridge comprises an abrasion resistant liner.

14. The system of claim 1, wherein the processor is further configured to calculate SG of the media based on the density.

15. The system of claim 1, further comprising a display device configured to display data obtained by at least one of the displacement device the temperature sensor, the pressure sensor, or the processor.

16. The system of claim 1, wherein the cartridge includes a conduit connecting the inflow media pipe and the outflow media pipe.

17. The system of claim 16, wherein the conduit has a low thermal expansion coefficient.

18. The system of claim 16, wherein the conduit is made of one or more layers of rubber or fiber.

19. The system of claim 18, wherein the fiber comprises KEVLAR.

20. The system of claim 16, wherein the conduit comprises one or more layers of reinforced rubber.

21. The system of claim 20, wherein the one or more layers of reinforced rubber is reinforced by a fiber.

22. The system of claim 16, wherein the conduit is reinforced by one or more rods extending about an axis coincident with the centerline of the conduit.

23. The system of claim 22, wherein the one or more rods comprise a plurality of rods equally spaced around the axis coincident with the centerline of the conduit.

24. The system of claim 16, wherein the conduit includes at least one high modulus beam or tube extending along the length of the conduit.

25. The system of claim 24, wherein the inflow media pipe and outflow media pipe are connected to an input and output of the cartridge via respective flanges, and the at least one beam or tube are affixed at each end to the flanges.

26. The system of claim 1, wherein the at least one high modulus tube or rod comprises a plurality of rods equally spaced around the axis coincident with the centerline of the conduit.

27. A system for continuously measuring density of a flowing media, comprising:
    a cartridge connected serially between an inflow media pipe and an outflow media pipe;
    a displacement sensing device adapted to monitor displacement changes of the cartridge when the media flow through the cartridge;
    a base configured to provide a support for the displacement sensing device;
    a plurality of supporting beams configured to support the inflow and outflow pipe;
    a pressure sensor;
    a temperature sensor;
    a processor configured to calculate density of the media based on measured displacement change, temperature and pressure; and
    an enclosure for housing the cartridge, the displacement sensing device, the base, the pressure sensor and the temperature sensor;
    at least one display device configured to present data obtained by the processor; and wherein the base and the plurality of supporting beams are connected to an underlying surface; and wherein the cartridge comprises a conduit positioned length-wise between the inflow and outflow pipes, the conduit including at least one high modulus tube or rod and a helical coil molded therein.

\* \* \* \* \*